United States Patent [19]
Berberich

[11] Patent Number: 5,739,430
[45] Date of Patent: Apr. 14, 1998

[54] RESISTIVE MOISTURE SENSOR

[75] Inventor: Reinhold Berberich, Frankfurt, Germany

[73] Assignee: VDO Adolf Schindling AG, Frankfurt, Germany

[21] Appl. No.: 649,131

[22] Filed: May 14, 1996

[30] Foreign Application Priority Data

May 24, 1995 [DE] Germany .................. 195 19 099.8

[51] Int. Cl.$^6$ .................................................. G01N 7/00
[52] U.S. Cl. ........................... 73/335.05; 73/29.01
[58] Field of Search .................. 73/24.04, 29.01, 73/335.02, 335.03, 335.05, 73

[56] References Cited

U.S. PATENT DOCUMENTS

| | | |
|---|---|---|
| 3,540,275 | 11/1970 | Diamond et al. .......... 73/335.02 |
| 4,797,605 | 1/1989 | Palanisamy .................. 324/689 |
| 4,805,070 | 2/1989 | Koontz et al. .............. 73/335.02 |
| 4,831,493 | 5/1989 | Wilson et al. .............. 73/335.02 |
| 5,040,411 | 8/1991 | Medzius ........................ 73/73 |

*Primary Examiner*—Elizabeth L. Dougherty
*Assistant Examiner*—Max H. Noori
*Attorney, Agent, or Firm*—Martin A. Farber

[57] ABSTRACT

In a moisture sensor in which electrodes are applied to a non-conductive support, preferably the windshield of a motor vehicle, and in which the resistance between the electrodes is a function of the quantity of moisture present on the support and on the electrodes, the electrodes consist of conductive paths of high electrical conductivity which are covered by a resistance layer of low electrical conductivity.

9 Claims, 2 Drawing Sheets

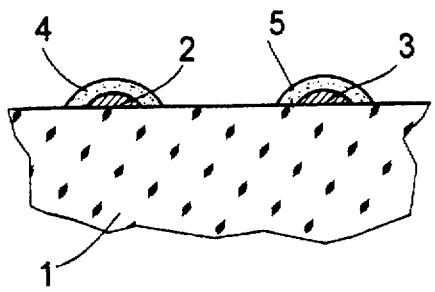
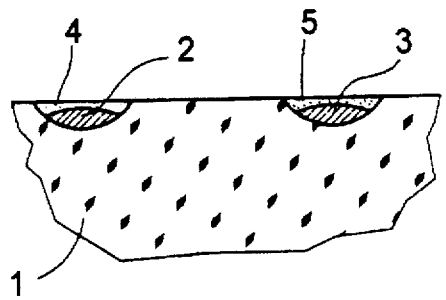
Fig.1  Fig.2
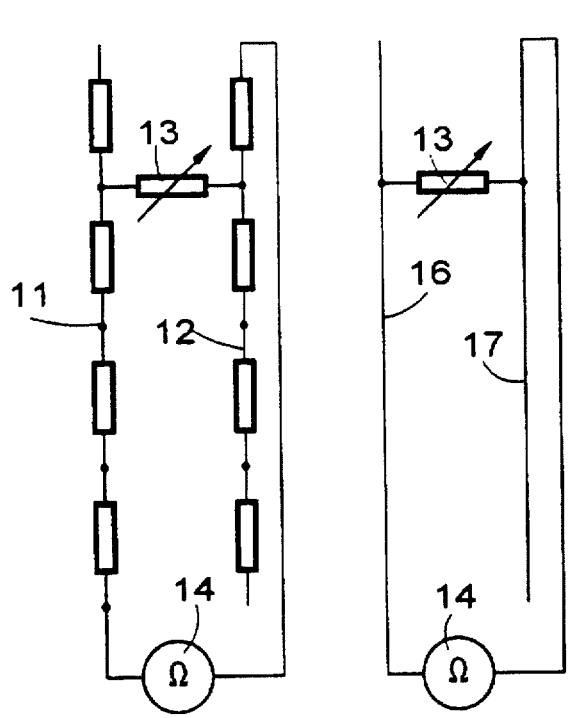
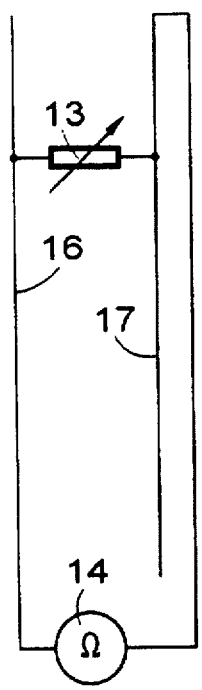
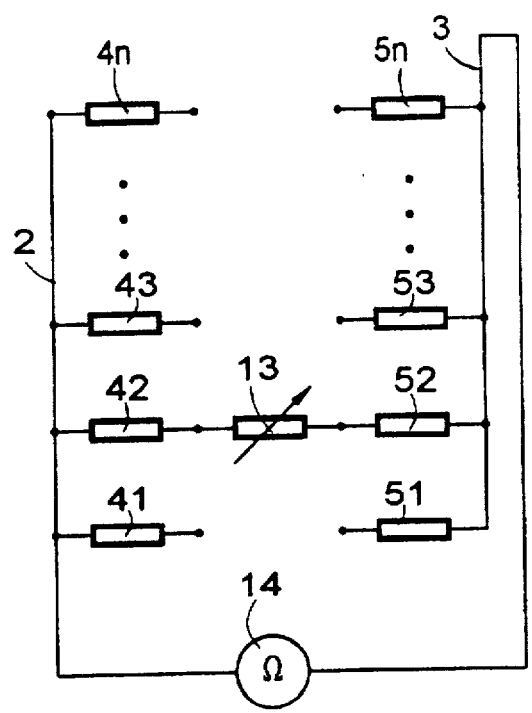
Fig.3a  Fig.3b  Fig.3c

1

RESISTIVE MOISTURE SENSOR

FIELD AND BACKGROUND OF THE INVENTION

The present invention relates to a moisture sensor in which electrodes are applied to a non-conductive support, preferably the windshield of a motor vehicle, and the resistance between the electrodes depends on the amount of moisture present on the support and the electrodes.

Resistive moisture sensors are used, for instance, to indicate moisture or drops of rain on the windshield of a motor vehicle so as automatically or semiautomatically to control the windshield wiper. For this purpose, conductive paths are arranged on the windshield or on some other suitable place so that the resistance between the conductive paths is reduced as a function of the amount of moisture incident thereon.

Resistance measurement circuits for evaluating this change in resistance are known. However, problems arise with them due to the fact that the change in resistance per amount of moisture, and in particular per drop, depends greatly on the composition of the impinging moisture. Thus, for instance, dissolved salts (thaw salts), acids (acid rain), as well as other admixtures (dirt, impurities, etc.) change the conductance of the moisture to be measured.

Thus, for instance, the change in resistance caused by one salt-containing drop as compared with a dry moisture sensor is substantially greater than that caused by a large number of drops of extremely pure water. Therefore, if a threshold for the start of wiping is so set that the wiping commences upon the presence of numerous raindrops which interfere with vision, the wiping will also be started if only a very few salt-containing drops come onto the windshield.

Furthermore, depending on the design of the moisture sensor and of the corresponding evaluation circuit, it is difficult to distinguish between one or more drops of good conductivity or, in the case of an overall low-ohm design, to recognize drops of low conductivity.

SUMMARY OF THE INVENTION

It is an object of the present invention to provide a moisture sensor the resistance of which is dependent inasmuch as possible on the amount of moisture or the number of drops and less on their specific conductivity.

According to the moisture sensor of the invention, the electrodes consist of conductive paths (2, 3) of high electrical conductivity, which are covered by a resistance layer (4, 5) of low electrical conductivity.

With the moisture sensor of the invention, in particular those amounts of moisture which are relevant for controlling windshield wipers can be dependably determined. By the resistance layer, the minimum obtainable resistance of the entirely wetted moisture sensor is accurately determined and limited. In this connection, sufficient sensitivity is retained to high-ohmic individual drops, since the resistance range to be measured is limited by the structural features of the moisture sensor. The moisture sensor of the invention thus supplies a signal which is approximately proportional to the wetted surface and substantially independent of the conductance of the impinging fluid.

In accordance with one feature of the invention, the conductive paths (2, 3) consist of metal and the resistance layers (4, 5) consist of sintered metal oxide. In this connection, the electrodes have a glass-like surface, as a result of which, on the one hand, a high resistance to abrasion is assured and, on the other hand, drops of moisture which are present there have the same tear-off behavior and the same shape as on the other part of the windshield. The measurement of the moisture with the moisture sensor of the invention accordingly takes place under conditions which apply also with respect to the limiting of vision due to the wetting of the windshield.

According to another feature of the invention, the resistance layers (4, 5) consist of ruthenium oxide.

The moisture sensor of the invention can also be developed in such a manner that there is a gradual transition between the conductivity of the conductive path and the resistance layer. This can be obtained, for instance, by the application of a single layer, in which connection assurance is had that, for instance, a coating having the desired variation in resistance is provided during the sintering process, i.e. that the conductive particles are present predominantly on the bottom and the glass particles predominantly on the top.

Ruthenium oxide has proven to be favorable as material for the resistance layers. One advantageous embodiment of the moisture sensor of the invention consists therein that the resistance layer (4, 5) has a resistivity of 10 $\Omega$m to 20 k$\Omega$m. The resistance layer preferably has a thickness of 0.5 µm to 100 µm. The conductive paths have a substantially lower resistance. If silver is used, a resistivity of 0.045 µ$\Omega$m is obtained.

Resistance pastes which are suitable for the moisture sensor of the invention, which can be printed on the support and on the conductive paths, are used in various manners by the thick-film technique and can be obtained on the market in a large number of resistivities. For this use, the printing pastes are characterized by a surface resistance which results, for a square resistance element of any size, in a normalized layer thickness. For the purpose of the present invention, there enter into consideration, with respect to the above-indicated range of resistivities, preferably printing pastes having surface resistances of between about 1 M$\Omega$ per square and about 1 G$\Omega$/square. The conductive path below same preferably has a resistance value of <10 $\Omega$/square. A silver conductive print known from the thick-film technique has a surface resistance of about 3 m$\Omega$/square.

A tight closing-off of the conductive paths by means of the resistance layer is established in particular in the manner that the resistance layers (4, 5) are wider than the conductive paths (2, 3) and gradually run out with respect to their thickness on the surface of the non-conductive support (1) alongside the conductive paths (2, 3). They seal the conductive paths (2, 3) off from the surroundings.

As an alternative, in the case of the moisture sensor of the invention, it can also be provided that the resistance layer (64, 69) covers the conductive paths (62, 63, 67, 68) and the surfaces of the support (61) between the conductive paths (62, 63, 67, 68). In this way, there is produced a uniform surface of the moisture sensor upon the application of which only its outer dimensions, but not the exact structures of the conductive paths need be taken into account.

Another variant of the moisture sensor of the invention is that the non-conductive support is a pane of glass (1), that the conductive paths (2, 3) lie in depressions in the surface of the pane of glass (1), and that the surfaces of the resistance layers (4, 5) lie essentially in the same plane as the surface of the pane of glass (1).

This variant has, in particular, the advantage that the wiping by the windshield wiper takes place in undisturbed manner in the same way as on the rest of the surface of the windshield. The depressions can be produced, for instance, by an etching process. Due to the slight depth of the depressions and the subsequent filling of them, weakening of the pane of glass need not be feared.

BRIEF DESCRIPTION OF THE DRAWINGS

The above and other objects and advantages in view, the present invention will become more clearly understood in connection with the detailed description of the preferred embodiments, when considered with the accompanying drawings, of which:

FIG. 1 is a cross section through a first embodiment;

FIG. 2 is a cross section through a second embodiment;

FIG. 3 comprising FIGS. 3, 3b and 3c shows equivalent circuit diagrams of wetted moisture sensors serving to explain the manner of operation of the invention;

DETAILED DESCRIPTION OF THE PREFERRED EMBODIMENTS

Figure 4:
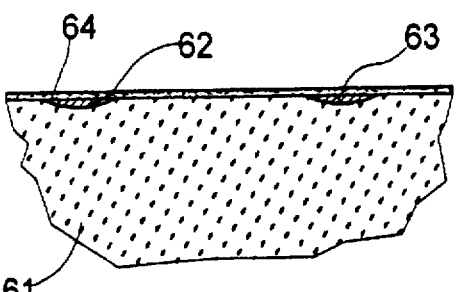
FIG. 4 is a cross section through a third embodiment.

Identical parts have been provided with the same reference numerals in the figures.

In FIGS. 1 and 2, the conductive paths and resistance layers are shown substantially exaggerated for greater ease in viewing. As can be noted from FIG. 4, two electrodes are developed in comb shape in order to form a moisture sensor having a sufficiently large surface. For the sake of simplicity, in FIGS. 1 and 2 only one strip of the two electrodes each has been shown.

On a windshield 1, only part of which has been shown, there are metallic conductive paths (or tracks) 2, 3 which are so covered by resistance layers 4, 5 that no moisture comes onto the conductive paths 2, 3.

The application of the conductive paths 2, 3 as well as of the resistance layers 4, 5 can be effected in simple manner by a printing process, whereby the glass pane with the layers applied thereon is brought to a temperature of about 600° C. in order to sinter the resistance layers 4, 5 onto it. For a resistance layer, ordinary commercial resistance pastes, particularly ones having a base of metal oxide, are suitable.

While, in the case of the embodiment shown in FIG. 1, the electrodes are applied onto the flat surface of the windshield 1, in the case of the example shown in FIG. 2, depressions have first of all been etched in the surface of the windshield 1 and the conductive paths 2, 3 and resistance layers 4, 5 have then been applied.

FIG. 3 shows electric equivalent circuit diagrams of moisture sensors which consist of electrodes of relatively low conductivity (FIG. 3a), of electrodes of relatively high conductivity (FIG. 3b), and of electrodes in accordance with the invention (FIG. 3c).

Electrodes 11, 12 of relatively low conductivity are shown in FIG. 3a as chains of resistors each of which has a value of 1 kΩ. One end of each of these resistor chains is connected to a resistance measuring device 14 which has been shown merely diagrammatically. A drop of water which contacts both electrodes is shown in the equivalent circuit diagram in the form of a variable resistor 13 since its value may vary from practically 0Ω up to the order of 100 kΩ depending on the content of salt in the water drop. The measured resistance value in this example is accordingly between 4 kΩ and 104 kΩ per water drop. Therefore 26 salt-free drops act equivalently to as one water drop having a high salt content.

Furthermore, in the case of the moisture sensor having the equivalent circuit diagram of FIG. 3a, the resistance changes only slightly when additional salt-containing drops contact the two electrodes. If, for instance, a single drop connects the electrodes 11, 12 at the beginning and end, there is then a total resistance of 2 kΩ, which then practically does not change any longer if further drops impinge between them.

In order to eliminate this last-mentioned disadvantage of the moisture sensor of FIG. 3a, electrodes 16, 17 of high conductivity can be used, in accordance with FIG. 3b. In this way, it is easier to distinguish whether one or more salt-containing drops are present. However, the ratio of the resistances between the electrodes in the case of salt-containing and salt-free drops is still substantially greater than in the case of the moisture sensor of FIG. 3a. If, for instance, one salt-containing drop has come onto the moisture sensor, it can practically no longer be determined with the moisture sensor whether it is raining.

The equivalent circuit diagram of FIG. 3c shows a moisture sensor in accordance with the invention, in which the conductive paths 2, 3 are connected to the resistance measurement device 14 and to resistors 41 to 4n and 51 to 5n. Each of the resistors represents a section or surface element of the resistance layer 4, 5 and each of them has values of 100 kΩ. If, for instance the sections formed by the resistors 42, 52 are connected together by a drop, then the measurable resistance results from a series circuit consisting of the resistor 42, the drop shown as potentiometer 13, and the resistor 52. Depending on the salt content and on the size of the water drop thereof, the drop can assume a resistance of about 0 Ω to 100 kΩ. For the total resistance there then results a value range of between 200 kΩ and 300 kΩ. In this way, it is clear that the dependence on the salt content has been substantially reduced in the moisture sensor of the invention as compared with the known moisture sensors.

FIG. 4 shows the cross-section through a part of a moisture sensor. The conductive paths 62 and 63 are applied on the windshield 61. Alternately the conductive paths 62 and 63 e.g. can also be formed by prior etching or fusing in the windshield 61. Both conductive paths 62 and 63 are covered or coated by one and the same resistance layer 64.

Figure 5:
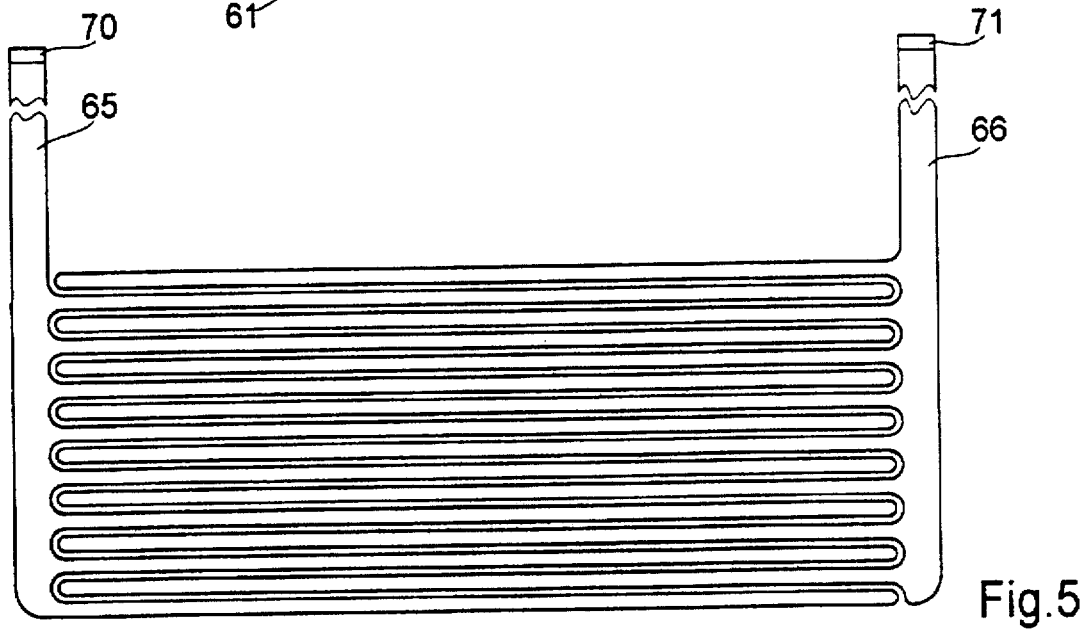
FIG. 5 is a plan view of a moisture sensor of the invention.

In the plan view of the moisture sensor according to FIG. 5, for formation of the moisture sensor, two electrodes 65 and 66 are formed in comb shape, on each of which is provided an electrical contact 70, 71 respectively for connection of the moisture sensor to an evaluation circuit.

Figure 6:
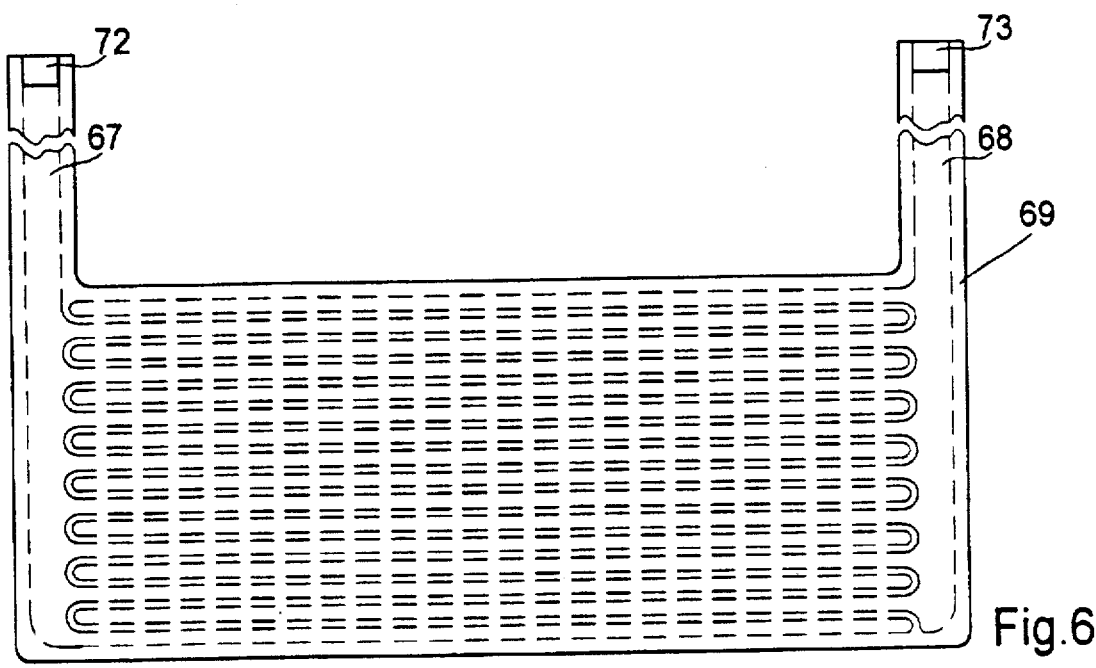
FIG. 6 is a plan view of another embodiment of moisture sensor in accordance with the invention.

A moisture sensor shown diagrammatically in FIG. 6 can for instance be developed in detail as follows. As resistance layer 69 there is used a layer of a 1-GΩ/square paste having a resistivity of 15 kΩm and a thickness of 4 μm. The conductive paths 67, 68 consist of 25 bars of a length of 12 cm and a width of 1 mm, their distance apart being 0.4 mm.

The resistance layer 69 overlays also here both electrodes 67 and 68. Via the electrical contacts 72 and 73, respectively, the electrodes 67 and 68 are connected with the evaluation circuit.

In the verticals, i.e. between a conductive path 67 or 68 and a drop present on the resistance layer 69, there results per $mm^2$ a passage resistance of $$R_v = 15000 \; \Omega m \times 4 \; \mu m / 1 \; mm^2 = 60 \; k\Omega$$

The resistance formed by the resistance layer 69 between the conductive paths 67 or 68—and therefore in horizontal direction—is designated below as offset resistance $R_O$ due to the displacement of the characteristic line between wetting and resulting resistance. For the dimensioning example indicated above, its size is:

$$R_O = [15000\ \Omega m \times 0.4\ mm]/[(25-1)] \times 120\ mm \times 4\ \mu m] = 520\ k\Omega.$$

If one proceeds from the basis that one drop already covers at least one square millimeter, and as a rule even more, then it becomes clear that the offset resistance $R_O$ does not impair the measurement as such but can be used to recognize a line break between the moisture sensor and an evaluation circuit.

In one advantageous development of the embodiment shown in FIG. 5, a 100 M$\Omega$/square paste is used, in which connection, in order to obtain the same vertical resistance, a layer thickness of 40 μm is required, whereby a higher resistance to scratching is established.

I claim:

1. A moisture sensor comprising a first electrode and a second electrode located on a non-conductive support, suitable for the windshield of a motor vehicle, wherein a resistance between the electrodes depends on an amount of moisture present on the support and the electrodes, and wherein each of said electrodes is comb shaped with a set of finger elements extending from a base element wherein the finger elements of the first electrode are interleaved with and spaced apart from the finger elements of the second electrode;

in each of the electrodes, the base element and the finger elements constitute electrically conductive paths and are covered by a resistance layer having an electrical conductivity which is low relative to the conductivity of the conductive paths;

in each of the electrodes, the resistance layer forms resistors at respective ones of the finger elements, the resistance layer serving to limit a minimum obtainable resistance of the moisture sensor upon a wetting of the entire sensor while retaining sensitivity to individual drops of moisture; and the base elements of the respective electrodes serve for connection to a resistance measuring device for measurement of the resistance between the electrodes.

2. A moisture sensor according to claim 1, wherein the conductive paths comprise metal and the resistance layers of the respective electrodes comprise sintered metal oxide.

3. A moisture sensor according to claim 1, wherein the resistance layers of the respective electrodes comprise ruthenium oxide.

4. A moisture sensor according to claim 1, wherein, at each of said electrodes, there is a gradual transition between conductivity of the conductive paths and the resistance layer.

5. A moisture sensor according to claim 1, wherein the resistance layer at an individual one of said electrodes has a resistivity in the range of 10$\Omega$m to 20 k$\Omega$m.

6. A moisture sensor according to claim 1, wherein the layer has a thickness of 0.5 μm to 100 μm.

7. A moisture sensor according to claim 1, wherein in each of the electrodes, the resistance layer wider than the conductive paths, and extends on the surface of the non-conductive support alongside the conductive paths to seal the conductive paths off from the environment.

8. A moisture sensor according to claim 1, wherein in each of the electrodes, the resistance layer covers the conductive paths and a surface of the support between the conductive paths.

9. A moisture sensor according to claim 1, wherein the non-conductive support is a pane of glass, the conductive paths lie in depressions in the surface of the pane of glass, and surfaces of the resistance layers of the respective electrodes lie essentially in a common plane with the surface of the pane of glass.

* * * * *